United States Patent
Wessels et al.

(10) Patent No.: US 8,092,899 B2
(45) Date of Patent: Jan. 10, 2012

(54) METHOD OF ACTIVATING A SILICON SURFACE FOR SUBSEQUENT PATTERNING OF MOLECULES ONTO SAID SURFACE

(75) Inventors: Jurina Wessels, Stuttgart (DE); William E. Ford, Stuttgart (DE); Akio Yasuda, Esslingen (DE)

(73) Assignee: Sony Deutschland GmbH, Cologne (DE)

( * ) Notice: Subject to any disclaimer, the term of this patent is extended or adjusted under 35 U.S.C. 154(b) by 45 days.

(21) Appl. No.: 12/173,490

(22) Filed: Jul. 15, 2008

(65) Prior Publication Data

US 2008/0280110 A1   Nov. 13, 2008

Related U.S. Application Data

(62) Division of application No. 11/003,805, filed on Dec. 3, 2004, now Pat. No. 7,427,477.

(30) Foreign Application Priority Data

Dec. 5, 2003 (EP) .................................. 03028132

(51) Int. Cl.
   *B32B 3/10* (2006.01)
(52) U.S. Cl. ................................. 428/195.1
(58) Field of Classification Search .......... None
   See application file for complete search history.

(56) References Cited

U.S. PATENT DOCUMENTS

| | | | |
|---|---|---|---|
| 4,716,103 A * | 12/1987 | Hunger et al. ................ 435/5 |
| 6,173,720 B1 | 1/2001 | Arndt et al. | |
| 6,354,309 B1 * | 3/2002 | Arndt et al. ................ 134/1.3 |
| 6,403,382 B1 | 6/2002 | Zhu et al. | |
| 7,259,258 B2 | 8/2007 | Kozlov et al. | |
| 2002/0037509 A1 * | 3/2002 | Arnold et al. ................ 435/6 |
| 2002/0137195 A1 | 9/2002 | Hamers et al. | |
| 2002/0142173 A1 | 10/2002 | Zhu et al. | |
| 2003/0042203 A1 | 3/2003 | Wormsbecher | |
| 2003/0047535 A1 * | 3/2003 | Schueller et al. ............. 216/41 |
| 2003/0081463 A1 * | 5/2003 | Bocian et al. ................ 365/200 |
| 2003/0119054 A1 * | 6/2003 | Mrksich et al. ............. 435/7.1 |
| 2006/0102935 A1 * | 5/2006 | Yitzchaik et al. ............ 257/253 |

FOREIGN PATENT DOCUMENTS

IL    152746    *  6/2003
JP    55-065150    *  5/1980

OTHER PUBLICATIONS

Xia et al: Soft Lithography Annual Review of Materials Science, Annual Reviews Inc., Palo Alto, CA, US, vol. 28, 1998, pp. 153-184, XP009023786.

X. Y. Zhu, et al., Grafting of High-Density Poly(Ethylene Glycol) Monolayers on Si(111), Langmuir 2001, 17, 7798-7803.

X.Y. Zhu, et al., "Molecular Assemblies on Silicon Surfaces via Si-O Linkages", Langmuir 2000, 16, 6766-6772.

(Continued)

*Primary Examiner* — Gerard Higgins
*Assistant Examiner* — Sathavaram I Reddy
(74) *Attorney, Agent, or Firm* — Oblon, Spivak, McClelland, Maier & Neustadt, L.L.P.

(57) ABSTRACT

The present invention relates to a method of activating a silicon surface for subsequent patterning of molecules onto said surface, and to patterns produced by this method, and further to uses of said pattern.

44 Claims, 8 Drawing Sheets

OTHER PUBLICATIONS

Younan Xia, et al., "Microcontact Printing of Octadecylsiloxane on the Surface of Silicon Dioxide and Its Application in Microfabrication", J. Am. Chem. Soc., 1995, 117, 9576-9577.

A. Teyssot, et al., Anodic grafting of organic groups on the silicon surface, Electrochimica Acta 47 (2002) 2565-2571.

Masato Ara, et al., "Friction force microscopy using silicon cantilevers covered with organic monolayers via silicon—carbon covalent bonds", Applied Physics Letters, vol. 83, No. 3, Jul. 21, 2003, pp. 578-580.

W. F. Bergerson, et al., "Assembly of Organic Mulecules on Silicon Surfaces via the SI-N Linkage", J. Am. Chem. Soc., 1999, 121, 454-455.

Jillian M. Buriak, "Organometallic chemistry on silicon surfaces: formation of functional monolayers bound through SI-C bonds", Chem. Commun., 1999, 1051-1060.

E. Delamarche, et al., "Transport Mechanisms of Alkanethiols during Microcontact Printing on Gold", J. Phys. Chem. B 1998, 102, 3324-3334.

Joel A. Haber, et al., Infrared and X-ray Photoelectron Spectroscopic Studies of the Reactions of Hydrogen-Terminated Crystalline Si(111) and Si(100) Surfaces with $Br_2$, $I_2$, and Ferrocenium in Alcohol Solvents, J. Phys. Chem. B 2002, 106, 3639-3656.

Noo Li Jeon, et al., Patterned polymer growth on silicon surfaces using microcontact printing and surface-initiated polymerization, Applied Physics Letters, vol. 75, No. 26, Dec. 27, 1999, pp. 4201-4203.

Yongseok Jun, et al., "Microcontact Printing Directly on the Silicon Surface", LANGMUIR, 2002, 18, 3415-3417.

J. Li, et al., "Visualization and Characterization of Poly(amidoamine) Dendrimers by Atomic Force Microscopy", LANGMUIR 2000, 16, 5613-5616.

Hong-Wei Li, et al., "Nanocontact Printing: A Route to Sub-50-nm-Scale Chemical and Biological Patterning", LANGMUIR 2003, 19, 1963-1965.

Ryan C. Major, et al., "Two-Step Approach to the Formation of Organic Monolayers on the Silicon Oxide Surface", LANGMUIR 2001, 17, 5576-5580.

B. Michel, et al., "Printing meets lithography: Soft approaches to high-resolution patterning", J. Res. & Dev. vol. 45 No. 5 Sep. 2001, 697-719.

T. Pompe, et al., "Submicron Contact Printing on Silicon Using Stamp Pads", LANGMUIR 1999, 15, 2398-2401.

E. Rogozhina, et al., Si-N linkage in ultrabright, ultrasmall Si nanoparticles, Applied Physics Letters, vol. 78, No. 23, Jun. 4, 2001, pp. 3711-3713.

H. Schmid, et al., Siloxane Polymers for High-Resolution, High-Accuracy Soft Lithography, Macromolecules 2000, 33, 3042-3049.

Pamela M. St. John, et al., "Diffraction-Based Cell Detection Using a Microcontact Printed Antibody Grating", Anal. Chem., 1998, 70, 1108-1111.

Younan Xia, et al., "Soft Lithography", Annu. Rev. Mater. Sci. 1998, 28:153-184.

* cited by examiner

METHOD OF ACTIVATING A SILICON SURFACE FOR SUBSEQUENT PATTERNING OF MOLECULES ONTO SAID SURFACE

CROSS-REFERENCE TO RELATED APPLICATIONS

This application is a divisional of U.S. application Ser. No. 11/003,805, filed on Dec. 3, 2004, which claims priority to EP 03 028 132.3, filed on Dec. 5, 2003.

FIELD OF THE INVENTION

The present invention relates to a method of activating a silicon surface for subsequent patterning of molecules onto said surface, and to patterns produced by this method, and further to uses of said pattern.

DISCUSSION OF THE BACKGROUND

The state of the art relevant to this invention falls into two general categories: 1) covalent modification of H-terminated Si surfaces, and 2) the μ-contact printing techniques. These two topics are summarized below.

A. Covalent Modification of H-Terminated Si Surfaces.

Many methods have been developed for attaching organic molecules to H-terminated Si surfaces via Si—C bond formation (Buriak, 2002, Chem. Rev. 102, 1271). These include:
1. Hydrosilylation involving a radical initiator.
2. Thermally induced hydrosilylation.
3. Photochemical hydrosilylation.
4. Hydrosilylation mediated by metal complexes.
5. Reactions of alkyl/aryl carbanions.
6. Electrochemical diazonium reactions.
7. [2+2] Reactions of alkynes and alkenes with reconstructed Si(100).
8. Diels-Alder ([4+2]) reactions of dienes with reconstructed Si(100).
9. Halogenation followed by alkylation.
10. Anodic grafting.

In addition, strategies have been developed for attaching organic molecules to H-terminated Si surfaces via Si—O—C or Si—N—C bond formation. These include:
1. Halogenation followed by reaction with alcohol or amine (Rogozhina, E. et al. (2001) Appl. Phys. Lett. 78, 3711; Zhu, et al. (2001) Langmuir 17, 7798).
2. Reaction with alcohol in the presence of halogen and one-electron oxidant (Haber, J. A.; Lewis, N. S. (2002) J. Phys. Chem. B 106, 3639).

B. Patterning, in Particular Microcontact Printing (μCP).

Presently, there are six techniques normally referred to as soft lithography: microtransfer molding, replica molding, micromolding in capillaries, solvent-assisted microcontact molding, near field phase shifted lithography and microcontact printing (also often abbreviated as μCP). The latter is the most commonly used and investigated soft lithography technique. For μCP, a liquid polymer precursor (usually polydimethylsiloxane, PDMS) is poured over a master that has been produced by photo- or electron beam lithography. After curing, the PDMS stamp with the desired pattern is peeled off the master (Xia and Whitesides, 1998, Annu. Rev. Mater. Sci. 28, 153). There are two possible methods of inking the stamp (Michel et al., 2001, IBM J. Res. & Dev. 5, 697): immersion inking and contact inking. For immersion inking, the stamp is inked with a solution and subsequently dried. For contact inking, the stamp is simply pressed on an inkpad, which is usually a block of PDMS that was previously treated with the ink solution. Subsequent pressing of the inked stamp on a substrate transfers the molecules contained in the ink from the stamp to the substrate.

The elasticity of the stamp is one of the parameters that determine the resolution limits of the soft-lithography (Michel et al., 2001, see above). Commercial PDMS, with a Young's modulus of 3 MPa, is too soft to define structures smaller than 500 nm. The hardness of the polymer can be changed by varying the ratio of pre-polymer to cross-linker and therefore the molecular mass $M_C$ between the cross-links or by mixing different types of polymer precursors (Schmid and Michel, 2000, Macromolecules 33, 3042). By using bimodal polymers having two populations of chain lengths, stamp materials with a Young's modulus of 9.7 MPa and sufficient toughness for large area printing can be made. Features as small as 80 nm can be achieved with these hard polymers. Currently the smallest feature size realized by μCP is <50 nm over 3×3 mm² using "hard" PDMS stamps and dendrimers as ink molecules (Li et al., 2003, Langmuir 19, 1963).

Another important factor determining the resolution limit of soft lithography to which much attention has been paid is diffusion of the ink molecules on the substrate surface. Several diffusion pathways of the ink molecules were considered (Delamarche et al., 1998, J. Phys. Chem. 102, 3324): simple spreading across the contact surface and diffusion from non-contact zones of the stamp to the surface, either along the stamp material or via the vapor phase. The molecular weight of the ink influences the vapor pressure and the diffusion path length. Higher molecular mass means lower diffusion and lower vapor pressure. In addition, the influence of ink concentration and printing time of contact has been investigated (Delamarche et al., 1998, see above).

Most μCP techniques for printing organic molecules onto silicon require a layer of silicon oxide in between, which introduces an electrically insulating barrier between the printed layer and the bulk silicon phase. On the other hand, most methods for attaching organic molecules directly to bulk silicon surfaces are not suitable for μCP. An exception is the process developed by Jun and Zhu (2002, Langmuir 18, 3415), but it requires the use of chlorine gas and the printing, which is performed in a glove-bag at 70° C., requires 30 minutes or longer.

Accordingly, it was an object of the present invention to provide for a method that allows for quick printing and/or patterning of molecules, preferably organic molecules onto silicon surfaces.

SUMMARY OF THE INVENTION

It was also an object of the present invention to provide for a printing method or patterning method that can be performed easily under ambient conditions and without the use of $Cl_2$.

It was furthermore an object of the present invention to provide for a microcontact printing technique for printing organic molecules onto silicon substrates, which yields good results in a shorter period of time than other prior art techniques.

Moreover, it was an object of the present invention to provide for a microcontact printing technique that allows the introduction of functional groups onto Si substrates.

All these objects are solved by a method of activating a silicon surface for subsequent patterning of molecules onto said surface, comprising the steps:
a) treatment of said silicon surface with HF,
b) treatment of said silicon surface resulting from a) with cyanuric chloride.

Preferably, the method further comprises the steps:
c) providing molecules to be patterned onto said silicon surface,
d) applying said molecules to be patterned onto said silicon surface resulting from step b).

In one embodiment, step b) is performed by exposing said silicon surface resulting from a) to cyanuric chloride, preferably to a solution of cyanuric chloride.

In one embodiment, said silicon surface resulting from step b) is exposed to cyanuric chloride, over its entire area or at least over a substantial part of its area involving also regions not intended to be covered by said molecules to be patterned, wherein, preferably, exposing said surface to cyanuric chloride occurs by immersion of said silicon surface into a solution of cyanuric chloride or by dripping or depositing a solution of cyanuric chloride onto said surface.

In this embodiment, preferably, steps c) and d) are performed by providing a stamp and inking said stamp, preferably by immersion inking or contact inking, with an ink containing said molecules to be patterned and optionally a solvent for said molecules, thereby producing an inked stamp,
placing said inked stamp on said silicon surface.

In another embodiment, step b) is performed by
ba) providing a stamp and inking said stamp, preferably by immersion inking or contact inking, with an ink that is a solution of cyanuric chloride, thereby producing an inked stamp,
bb) placing said inked stamp on said silicon surface, wherein, preferably, said ink does not comprise said molecules to be patterned on said silicon surface.

Preferably, bc) said inked stamp is withdrawn from said silicon surface.

In this other embodiment, preferably, after step bc),
bd) said silicon surface is rinsed with a solvent, preferably an inert solvent.

More preferably, after step bd), steps c) and d) are performed by exposing said silicon surface to said molecules to be patterned, preferably to a solution of said molecules, wherein, preferably, said silicon surface is exposed to said molecules to be patterned, over its area entire area or at least over a substantial part of its area involving also regions not intended to be covered by said molecules to be patterned.

Preferably, exposing said silicon surface to said molecules to be patterned, occurs by immersion of said silicon surface into a composition, preferably a solution, of said molecules, or by dripping or depositing said molecules onto said surface.

In both embodiments, preferably, step b) occurs in the presence of a base.

Preferably, said molecules to be patterned are molecules containing nucleophilic groups, preferably with active hydrogen atoms, wherein, more preferably, said molecules containing nucleophilic groups are in solution and at a concentration in the range of 1 µM-100 mM.

In one embodiment said molecules containing nucleophilic groups are selected from the group comprising ammonia, primary amines, secondary amines, water, alcohols, phenols, thiols and mercaptans.

In one embodiment, said immersion inking is achieved by immersing said stamp into said ink or by placing said ink onto said stamp.

In one embodiment, said contact inking is achieved by placing said stamp on an ink pad that has previously been treated with said ink, or by placing an ink pad that has previously been treated with said ink onto said stamp.

In a preferred embodiment, said stamp is made of an elastic material having a Young's modulus in the range of 1 MPa to 50 MPa, preferably 1 MPa to 20 MPa, more preferably 2 MPa to 15 MPa.

Preferably, the method according to the present invention comprises the additional steps:
e) leaving said inked stamp on said silicon surface for a time in the range of 1 s to 12 h, preferably 1 s to 200 s, more preferably 1 s to 100 s and, optionally, applying pressure onto said inked stamp,
f) withdrawing said stamp from said silicon surface.

Preferably, the method according to the present invention furthermore comprises the additional steps, which occur after d) and, in the embodiment comprising step f):
g) rinsing said silicon surface with a solvent, preferably a solvent that is also present in said ink, more preferably an inert solvent,
h) exposing said silicon surface to compounds containing nucleophilic groups, preferably with active hydrogen atoms, more preferably selected from the group comprising ammonia, primary amines, secondary amines, water, alcohols, phenols, thiols and mercaptans, to passivate said silicon surface, or to introduce functional groups into said silicon surface.

In one embodiment, said silicon surface used for a) has been pre-patterned with gold electrode structures.

Preferably, said silicon surface has a (100) or (110) or (111) surface orientation, wherein, more preferably, said silicon surface has a native or thermally grown oxide layer on it.

In one embodiment, said silicon surface is part of a silicon substrate that is doped (n-type or p-type) or undoped.

In one embodiment, said treatment of said silicon surface with HF (step a)) is done by treating said silicon surface with aqueous HF that may contain HCl, wherein, preferably, said aqueous HF has a concentration that lies in the range of 0.06 M to 6 M, preferably approximately 0.6 M, and said HCl has a concentration that lies in the range of 0.01 to 10 M, preferably 0.01 M to 1 M.

Preferably, said treatment with aqueous HF occurs for 0.1-10 minutes, preferably at 0° C. to 90° C., more preferably 10° C. to 40° C.

Preferably, a treatment with aqueous HF is performed if said silicon surface has a (100) or (110) surface orientation.

In another embodiment, said treatment of said silicon surface with HF is done by treating said silicon surface with aqueous $NH_4F$ that may contain $NH_4OH$, wherein, preferably, said aqueous $NH_4F$ has a concentration that lies in the range of 0.1-11 M, preferably approximately 2 M, and said $NH_4OH$ has a concentration that lies in the range of 0.01 M to 10 M.

Preferably, said treatment with aqueous $NH_4F$ occurs for 0.1-10 min, preferably at 0° C. to 90° C., more preferably 10° C. to 40° C.

Preferably, a treatment with aqueous $NH_4F$ is performed if said silicon surface has a (111) surface orientation.

In one embodiment, said treatment with cyanuric chloride (step b)) is performed using a solution of cyanuric chloride, preferably having a concentration in the range of from 0.1-10 wt. %, wherein, preferably, said treatment with cyanuric chloride is performed over 1-100 min, preferably at 0-50° C.

In one embodiment, said base is selected from the group comprising sterically hindered tertiary organic amines or phosphazene bases, preferably N-ethyldiisopropylamine, N,N-diisopropylisobutylamine, tributylamine, 2,2,6,6-tetramethylpiperidine, N,N,N',N'-tetramethyl-1,8-naphthalenediamine, 2,4,6-tri-tert-butylpyridine, tert-butylimino-tris-(dimethylamine)-phosphorane, or tert-butylimino-tripyrrolidino-phosphorane, wherein, preferably, said base has a concentration in the range of 0% to 10 wt. %.

In one embodiment, said molecules containing nucleophilic groups, preferably with active hydrogen atoms, are selected from the group comprising ammonia, primary amines, secondary amines, water, alcohols, phenols, thiols and mercaptans.

The objects of the present invention are also solved by a pattern of molecules on a silicon surface produced by the method according to the present invention.

The objects of the present invention are also solved by the use of the pattern according to the present invention in an electronic device, a memory device, a photonic device, an energy conversion device, a display device, a sensor device, a biochip, an actuator, an electromechanical device or a microfluidic device.

The objects of the present invention are furthermore solved by the use of cyanuric chloride to activate a silicon surface for subsequent patterning of molecules onto said silicon surface, preferably by performing the method according to the present invention.

In one embodiment, the silicon surface to be activated by cyanuric chloride is H-terminated.

The objects of the present invention are also solved by an activated silicon surface produced by the use according to the present invention or produced by the method according to the present invention, wherein preferably the activated silicon surface, after activation by cyanuric chloride, is still H-terminated in a proportion of its surface area.

The objects of the present invention are furthermore solved by an activated silicon surface, preferably as described in the previous sentence, to which 2,4-dichloro-triazine is covalently linked.

Furthermore the objects of the present invention are solved by the use of an activated silicon surface according to the present invention for the fabrication of an electronic device, a memory device, a photonic device, an energy conversion device, a display device, a sensor device, a biochip, an actuator, an electromechanical device or a microfluidic device.

As used herein, the term "microcontact printing" is meant to designate any process useful for applying an ink onto a surface, preferably such that the dimensions of the printed structures lie in the μm-range, more preferably in the nm-range. As outlined above, microcontact printing as such is a process well known to someone skilled in the art. As used herein, "microcontact printing" can also be used interchangeably with simply "printing", albeit on a μm-scale or nm-scale. The term "patterning", as used herein, is sometimes used herein as a more general term. It is meant to designate any process by which a pattern of molecules can be generated on a surface. One way of achieving this is on a nm-to-μm-scale is microcontact printing.

The term "inert", when used herein in connection with a solvent, is meant to indicate that the solvent is not likely to undergo a chemical reaction, in particular not any reaction with cyanuric chloride and/or a reaction with the silicon surface activated by cyanuric chloride.

As used herein, the term "cyanuric chloride" is meant to designate the compound 2,4,6-trichloro-triazine, wherein the nitrogen atoms are preferably distributed in a symmetric(s) manner, i.e. 2,4,6-trichloro-s-triazine or, interchangeably 2,4,6-trichloro-1,3,5-triazine.

The process according to the present invention is easy and quick to perform and allows for the fabrication of patterns that are comparable to standard soft lithography techniques.

The present invention provides a quick process for patterning, in particular microcontact printing of molecules under ambient conditions onto doped or undoped Si surfaces with a native or thermally grown oxide surface. The substrate is silicon, preferably Si(100) or Si(110) or Si(111), doped (n- or p-type) or undoped, with native or thermally-grown oxide layer on the surface. The process is described below. In one embodiment, it involves in the first step a treatment with a dilute HF solution in order to create a H-terminated surface (Step 1). In the second step the H-terminated surface is treated with cyanuric chloride, preferably a solution thereof, resulting in an activated Si surface (Step 2). Step 2 may be facilitated by addition of a base such as N-ethyldiisopropylamine. In a preferred embodiment, the activated substrate is subsequently used for the pattern transfer process from a stamp. As ink, any molecule containing a nucleophilic group, such as an amine, alcohol, or thiol, is suitable, preferably selected from the group comprising ammonia, primary amines, secondary amines, water, alcohols, phenols, thiols and mercaptans. The concentration of the ink is typically in the range 0.1-100 mM and either contact inking or solution inking can be used (Step 3). The pattern transfer step involves placement of the inked stamp on the substrate (Step 4). In case the stamp is fabricated from a siloxane elastomer (Sylgard 184, Dow Corning), the material is soft enough (Young's modulus of 3 MPa) to provide a good contact between the stamp and the substrate. If the stamp has a larger Young's modulus (~9-10 MPa) additional pressure may be needed in order to establish a sufficient contact between the substrate and the stamp. The required additional pressure depends on the size of the printed structures (Michel et al., 2001, see above). The time necessary for the pattern transfer depends on the width of the transferred patterns, the molecular weight of the ink molecule, and the substrate/molecule interaction. Printing times are typically between 1 s and 100 s. In the post-printing process, the substrate is thoroughly rinsed with the solvent that was used for the ink in order to remove excess and non-specifically absorbed ink material from the substrate. Exposing the printed substrate to molecules containing nucleophilic groups, preferably selected from the group comprising ammonia, primary amines, secondary amines, water, alcohols, phenols, thiols and mercaptans, can passivate the remaining activated Si surface or introduce new functionalities. Three examples of the printing/patterning process are described below, either without (Example 1) or with N-ethyldiisopropylamine as base (Examples 2 and 5). The control experiments are described in Example 3 and 4.

Process parameters of currently preferred embodiments of the method according to the present invention:

Substrates: Silicon substrates, preferably Si(100) or Si(110) or Si(111), doped (n- or p-type) or undoped, with native or thermally-grown oxide layer on surface.

1. HF treatment:
    Si(100) or Si(110): Treatment with aqueous HF (0.6 M [0.06-6 M]) that may contain HCl (0.01-10 M) for 0.1-10 min at 0° C. to 90° C., preferably 10° C. to 40° C.
    Si(111): Treatment with aqueous $NH_4F$ (2 M [0.1-11 M]) that may contain $NH_4OH$ (0.01-10 M) for 0.1-10 min at 0° C. to 90° C. preferably 10° C. to 40° C.
2. Surface activation with cyanuric chloride: Treatment with a solution of cyanuric chloride (0.1-10 weight percent) that may contain base (0-10 weight percent) for 1-100 min at 0-50° C.
3. Inking process: A solution-inking or contact-inking process is used, depending on the type of ink. The concentration of the ink depends on the type of inking process, the composition of the ink, and the desired resolution of the printed structure.

4. Pattern transfer: The parameters for the pattern transfer depend on the type of inking process, the composition of the ink, the Young's modulus of the stamp, and the desired resolution of the printed structure.
5. Post-printing/post-patterning process: Rinsing with solvent, preferably the one used in the ink. Those parts of the substrate that are still activated may be treated with a solvent or solution containing nucleophilic compounds to passivate them or to introduce new functionalities.

It is also possible to apply the above-described processes to silicon substrates that have been pre-patterned with gold electrode structures. The electrode structures are not destroyed by the HF treatment (Example 6).

It is further possible to pattern H-terminated Si surfaces by exchanging the order of Step 2 and Step 3. In this case, a solution of cyanuric chloride with or without base is used as the ink. However, the PDMS stamp may be chemically altered, causing a change of its Young's modulus. Such stamps may not be reusable, and the process parameters may have to be adjusted in such a way that the ink-induced changes in the stamp do not affect the pattern transfer process. The patterned substrate is subsequently rinsed thoroughly with an inert solvent. This process results in the patterned regions of activated surface, which can then be reacted with molecules containing nucleophilic groups. An example of this process is described below (Example 5).

In the method of the present invention, the function of cyanuric chloride, either alone or combined with a base, is to activate hydrogen-terminated silicon surfaces toward reaction with nucleophilic reagents. While not wishing to be limited by theory, the mechanism of activation is likely to involve one or both of two processes shown in FIG. 1. In one of these processes, the triazine nucleus of cyanuric chloride (in the form of the 2,4-dichloro-s-triazine moiety) remains attached to the silicon surface, with elimination of HCl (FIG. 1 A). In the other process, cyanuric chloride serves as a chlorinating agent, with elimination of the resulting triazine compound (FIG. 1 B). A base such as a tertiary organic amine may facilitate the first of these processes by neutralizing the HCl that is produced.

While not wishing to be limited by theory, the activated silicon surfaces may react with nucleophilic reagents with the release of chloride (FIG. 2). In the examples shown in FIG. 2, the nucleophilic reagent is a primary amine containing an additional functional group X, $H_2N-R-X$, where R is a saturated or unsaturated hydrocarbon moiety. The dichlorotriazine-terminated silicon surface created in the first process (FIG. 1A) can react with the nucleophilic reagent to replace one or both chlorine atoms of the triazine nucleus, as shown in FIGS. 2A and B. The replacement of both chlorine atoms can be performed in two steps using different nucleophilic reagents (FIG. 2C). The chlorine-terminated silicon surface created in the second process (FIG. 1B) can react with the nucleophilic reagent to form a bond directly between the silicon and the nucleophile (FIG. 2D). Groups having different functionalities (e.g., positive or negative charge, redox activity, photoluminescence, etc.) can be introduced onto the modified silicon surface by varying the nature of the functional group X.

The processes described above for surface-chemical modification/functionalization of silicon are utilized in the present invention for microcontact printing/patterning on planar silicon substrates, but the inventors also recognize the utility of said processes for surface-chemical modification/functionalization of micro- and nano-structured forms of silicon. Micro- and nano-structured forms of silicon that can be processed in this manner include porous silicon, silicon nanoparticles and nanowires, and silicon tips for scanning probe microscopy. These materials are being developed for various biological, electronic, and optical applications, including photoluminescent biological markers, sensors, non-volatile floating gate memories, and optical interconnects. Surface-chemical modification/functionalization of silicon is required for many of these applications to provide stability and/or dynamic range and/or for integration with other materials and/or components. The processing represented in FIG. 1 and FIG. 2 provides a general means for accomplishing the necessary surface chemistry to those who are familiar with the art.

BRIEF DESCRIPTION OF THE FIGURES

Reference is now made to the figures, wherein.

The invention will now be further described by the following examples, which are given to illustrate the invention, not to limit it.

EXAMPLES

Example 1

Figure 1:
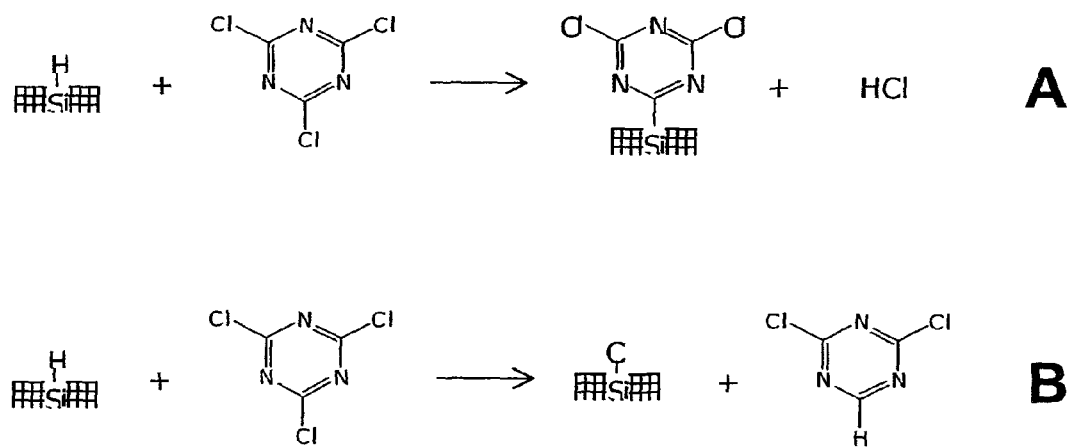
FIG. 1 shows a possible mechanistic explanation of activation of hydrogen-terminated silicon surfaces by cyanuric chloride according to the present invention.
Figure 2:
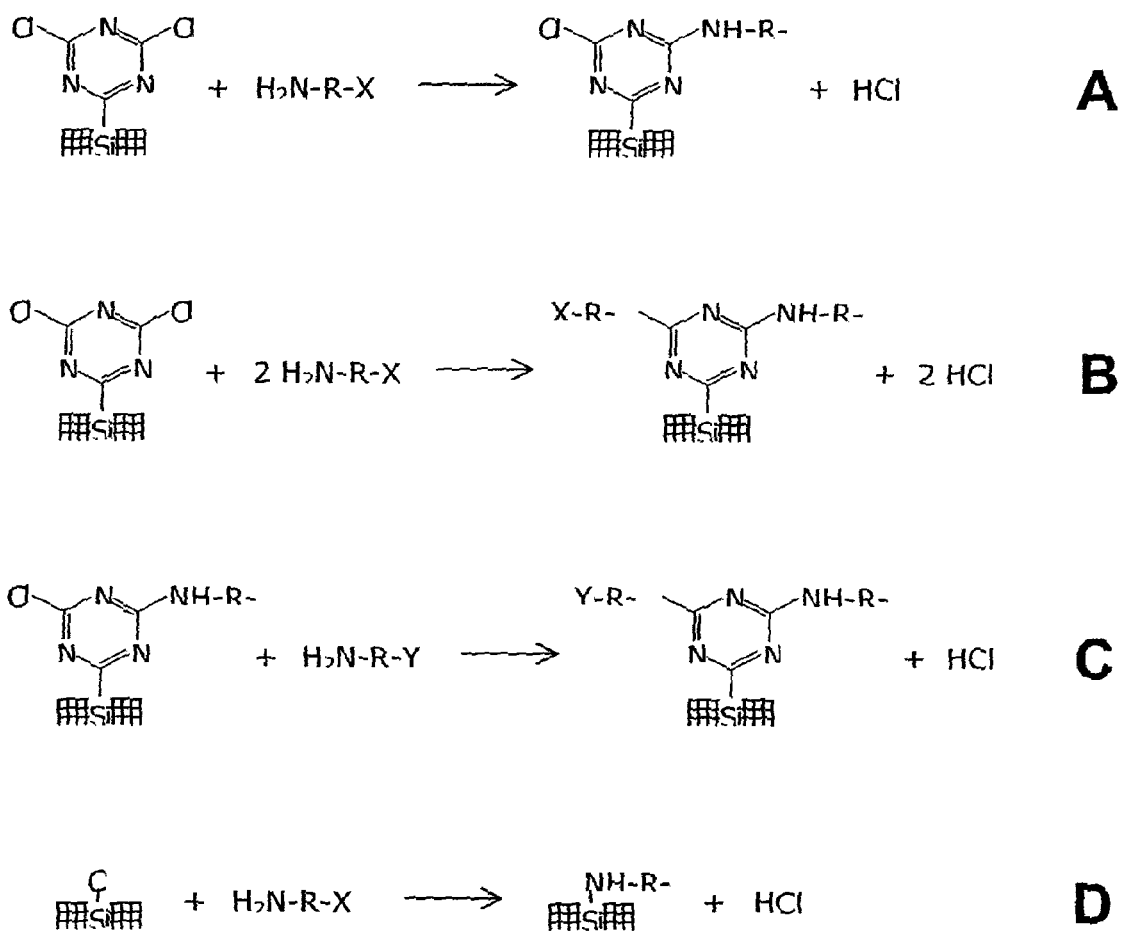
FIG. 2 shows a possible mechanistic explanation of the further reaction of activated silicon surfaces with nucleophilic reagents.
Figure 3:
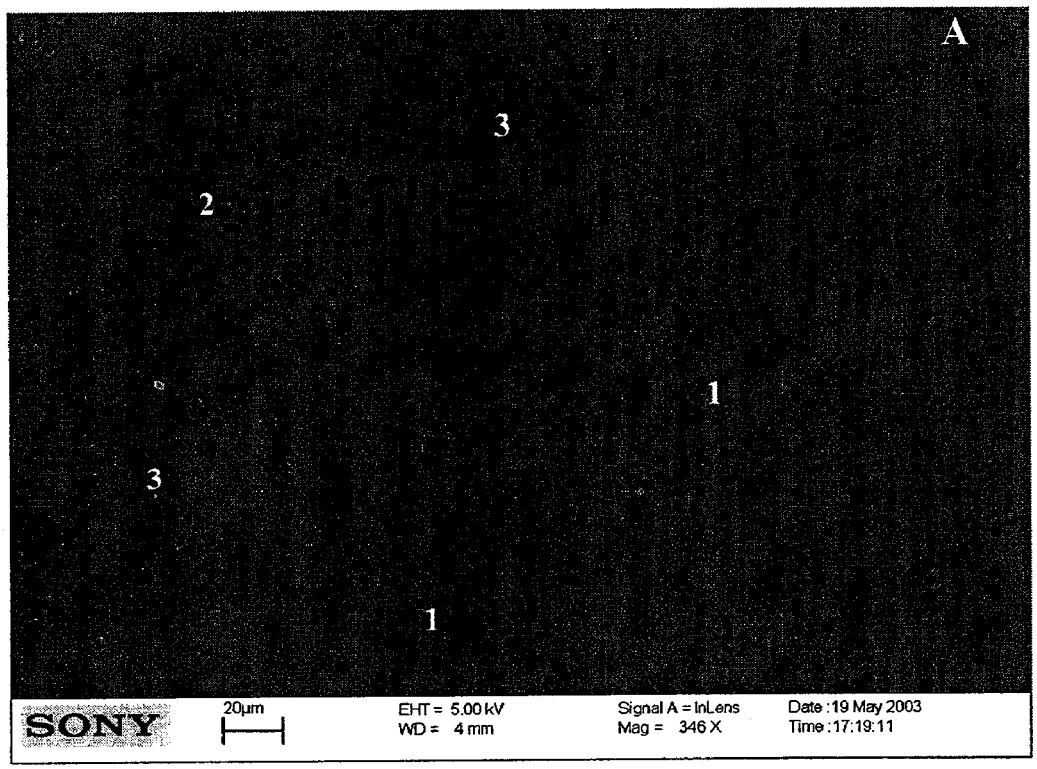
FIG. 3: Panel (A) shows an SEM image of the transferred pattern of Example 1 (scale bar 20 µm). Panel (B) shows a magnification of the image showing the electrode bars and gaps (scale bar 3 µm).
Figure 3:
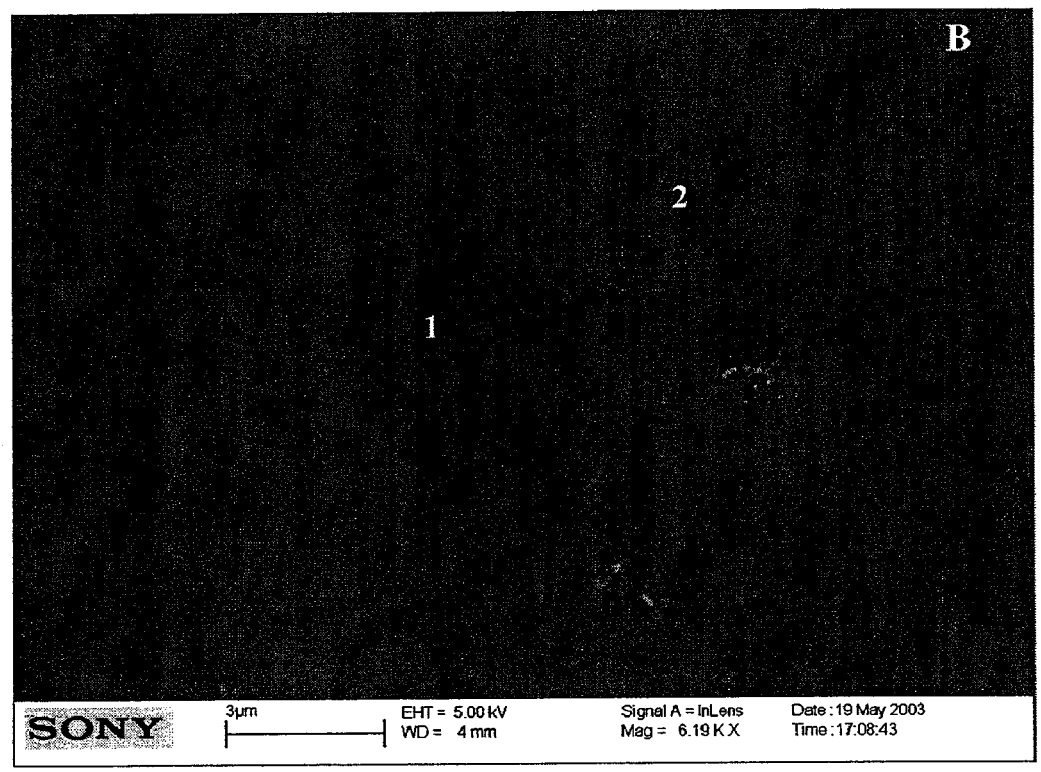
Figure 4:
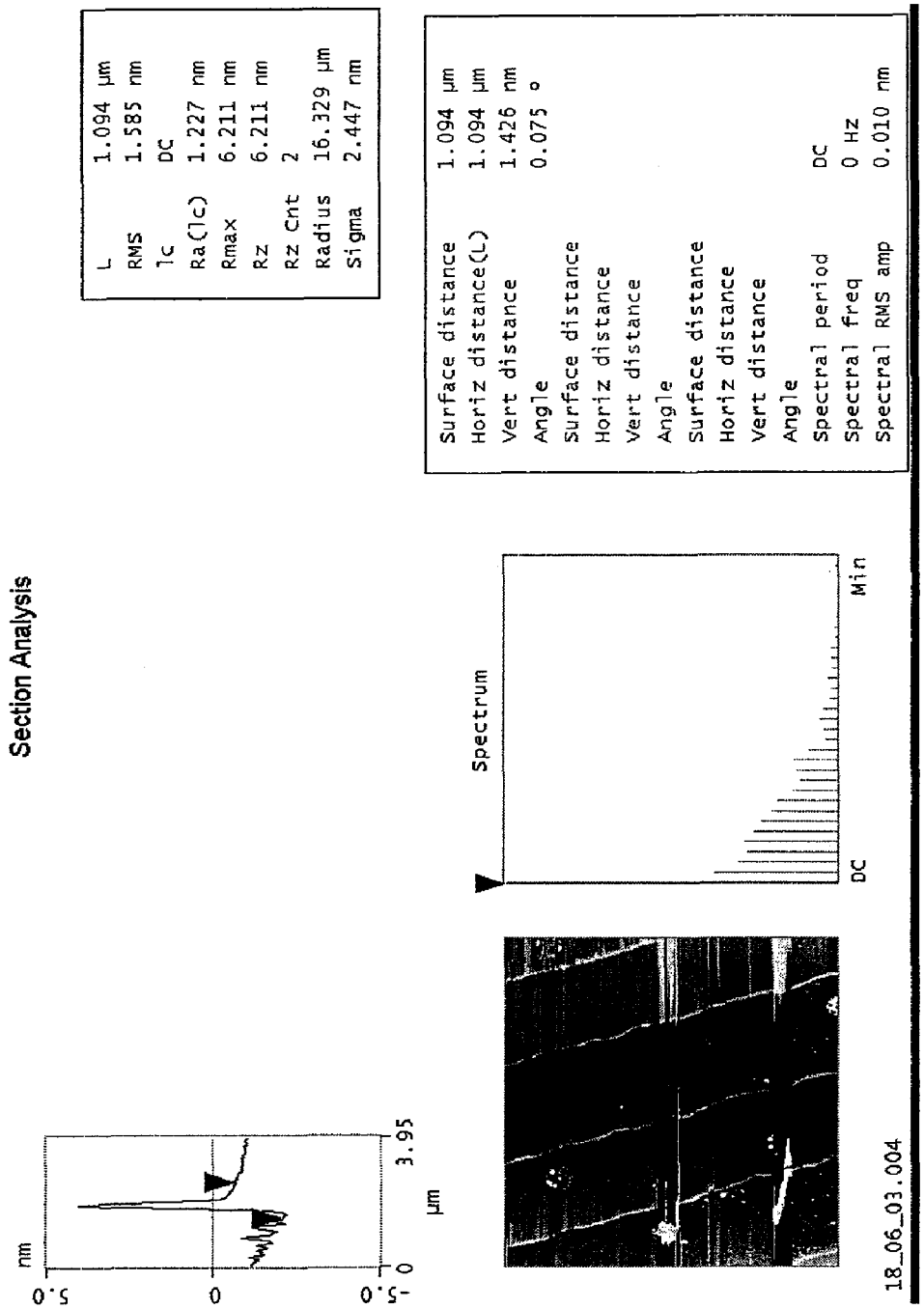
FIG. 4 shows a section analysis of the AFM image of the transferred pattern of Example 1. The height of the edge of the bar is ~4 nm and the height in the center of the bar is ~1.5 nm.

A Si(100) substrate (n-doped with native oxide surface) was treated in the $O_2$-plasma etcher for 5 min at 0.3 mbar. Subsequently it was dipped for 1 min in a HF solution (HF:$H_2O$ 1:50) and dried with compressed air (Step 1). The substrate was treated for 10 min with a solution of cyanuric chloride (100 mg in 900 µl acetone) and subsequently washed with acetone and dried with compressed air (Step 2). The solution inking process was used for inking of the stamp (Step 3). A PDMS stamp (Sylgard 184, Dow Corning) was placed for 10 min into an amine-terminated dendrimer ink solution and dried with compressed air. The ink solution was prepared by diluting 10-fold a commercially available solution of the dendrimers (Starburst® (PAMAM) Dendrimer, Generation 4, 10 wt. % solution in methyl alcohol, calculated FW 14,215, from Aldrich Chemical Co., Product #41,244-9). Subsequently the stamp was placed on the modified silicon substrate for 10 min (Step 4). Afterwards the sample was thoroughly rinsed with methanol and dried with compressed air (Step 5). FIG. 3 shows SEM images of the transferred pattern, which consists of an interdigitated electrode structure having gaps and electrodes with a width of 5 µm. FIG. 3A shows the printed contact pads (1), the printed electrodes (2) and structures with rounded edges (3) that result from stamp material that adhered to the surface during the printing process. This unspecific adhesion takes place because the distances between the printed structures are too large. FIG. 3B shows a magnification of the electrodes with the gaps (1) and the bars (2). FIG. 4 shows a section analysis of an AFM image of the printed structure. The height on the edge of the printed structure is ~4 nm, while the average height in the center of the structure is ~1.5 nm. The theoretical diameter of the dendrimer is about 4.5 nm. It is well known that the observed diameters of dendrimers that are immobilized on surfaces are usually much smaller due to surface interactions which leads to flattening of the molecules (Lie et al., 2000, see above). Thus the height in the centre of the bars most likely corresponds to a monolayer of dendrimers, while at the edges additional material accumulates. The formation of hillocks has also been described in the literature and attributed to access ink on the stamp (Pompe et al., 1999, Langmuir 15, 2398).

Example 2

Figure 5:
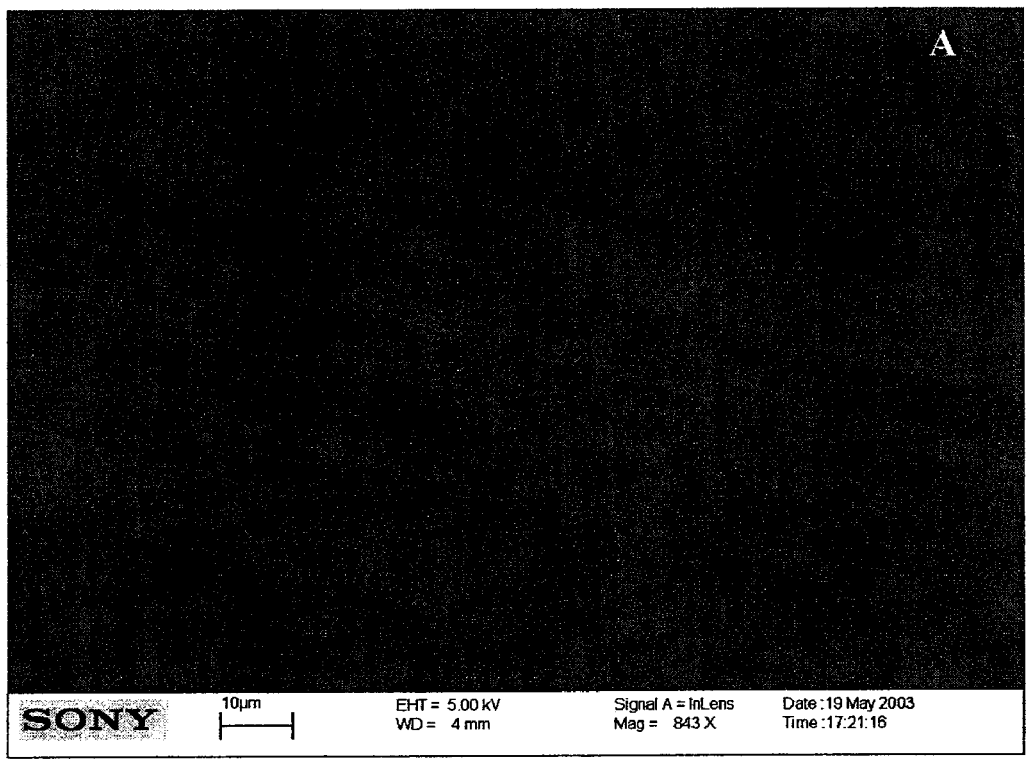
FIG. 5: Panel (A) shows an SEM image of the transferred pattern of Example 2 (scale bar 10 µm). Panel (B) shows a magnification of the image showing the electrode bars and gaps (scale bar 2 µm).
Figure 5:
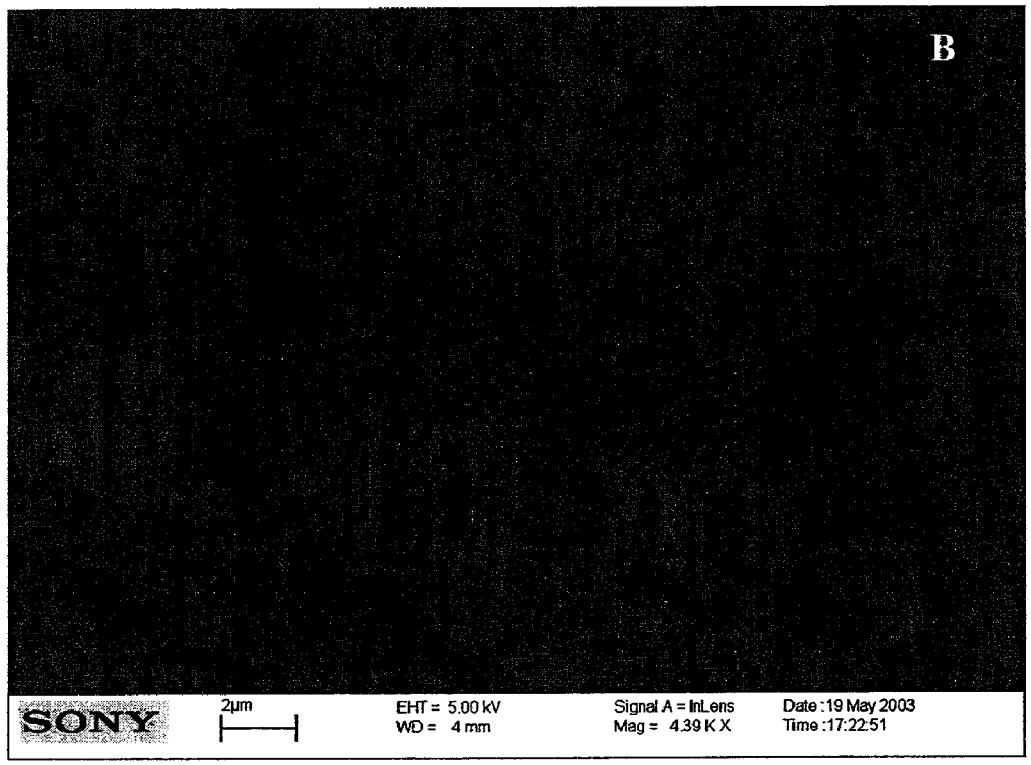

A Si(100) substrate (n-doped with native oxide surface) was treated in the $O_2$-plasma etcher for 5 min at 0.3 mbar. Subsequently it was dipped for 1 min in a HF solution (HF: $H_2O$ 1:50) and dried with compressed air (Step 1). The substrate was treated for 10 min with a solution of cyanuric chloride and N-ethyldiisopropylamine in acetone (100 mg cyanuric chloride, 100 µl N-ethyldiisopropylamine in 800 µl acetone) and subsequently washed with acetone and dried with compressed air (Step 2). The solution inking process was used for inking of the stamp (Step 3). A PDMS stamp (Sylgard 184, Dow Corning) was placed for 10 min into an amine-terminated dendrimer ink solution and dried with compressed air. The ink solution was prepared by diluting 10-fold a commercially available solution of the dendrimers (Starburst® (PAMAM) Dendrimer, Generation 4, 10 wt. % solution in methyl alcohol, calculated FW 14,215, from Aldrich Chemical Co., Product #41,244-9). Subsequently the stamp was placed on the modified silicon substrate for 10 min (Step 4). Afterwards the sample was thoroughly rinsed with methanol and dried with compressed air (Step 5). FIG. 5 shows SEM images of the transferred pattern, which is the same as in Example 1. FIG. 5A shows an SEM image of the transferred electrode bars. In FIG. 5B (magnified view of FIG. 5A) it is clearly visible that the edges of the electrode bars are fuzzy. This is probably due to the presence of N-ethyldiisopropylamine in the ink, which may enhance the diffusion of the ink and also distort the PDMS stamp.

Example 3

Control

Figure 6:
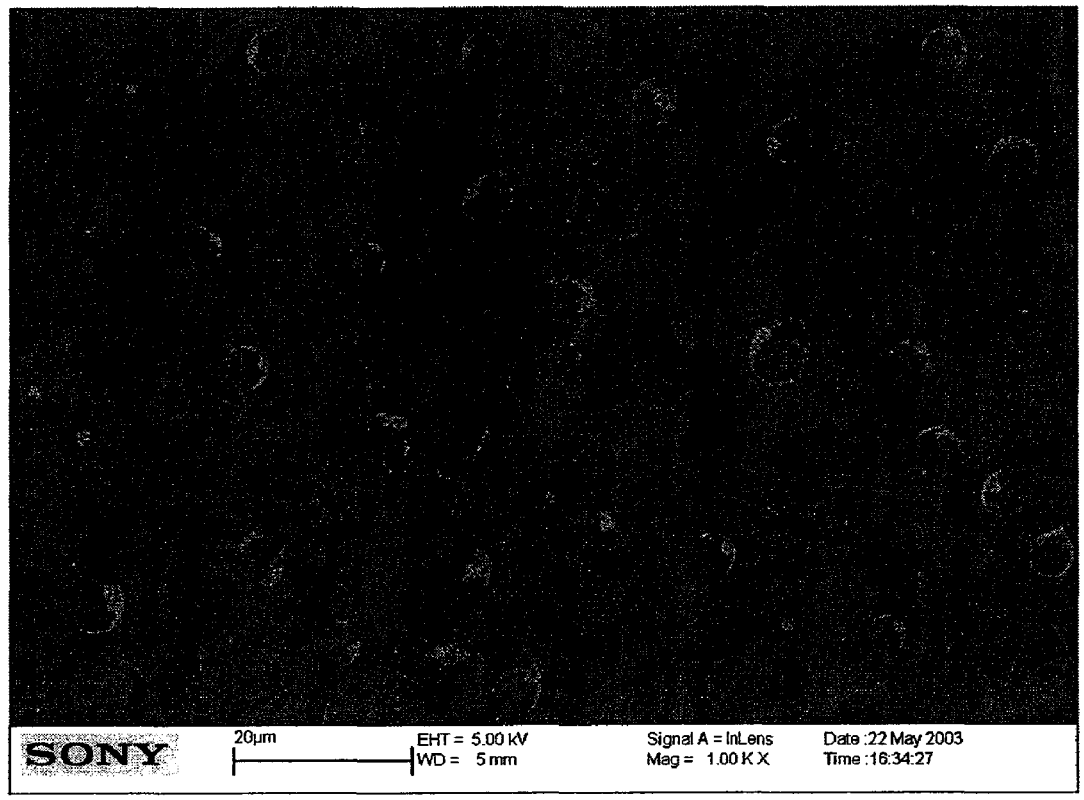
FIG. 6 shows an SEM image of the substrate from Example 3 (control) (scale bar 20 µm).

A Si(100) substrate (n-doped with native oxide surface) was treated in the $O_2$-plasma etcher for 5 min at 0.3 mbar. Subsequently it was dipped for 1 min in a HF solution (HF: $H_2O$ 1:50) and dried with compressed air (Step 1). The substrate was exposed for 10 min. to a solution of 100 mg cyanuric chloride and 900 µl acetone. Afterwards the substrate was thoroughly washed with acetone and dried with compressed air (Step 2). A PDMS stamp that was not inked was placed on the substrate for 10 min (Step 4). Afterwards the substrate was washed with methanol and dried with compressed air (Step 5). As can be seen from FIG. 6, no pattern was transferred to the substrate. This control experiment demonstrates that a nucleophilic reagent such as amine-terminated dendrimer is preferably used for developing the pattern.

Example 4

Control

Figure 7:
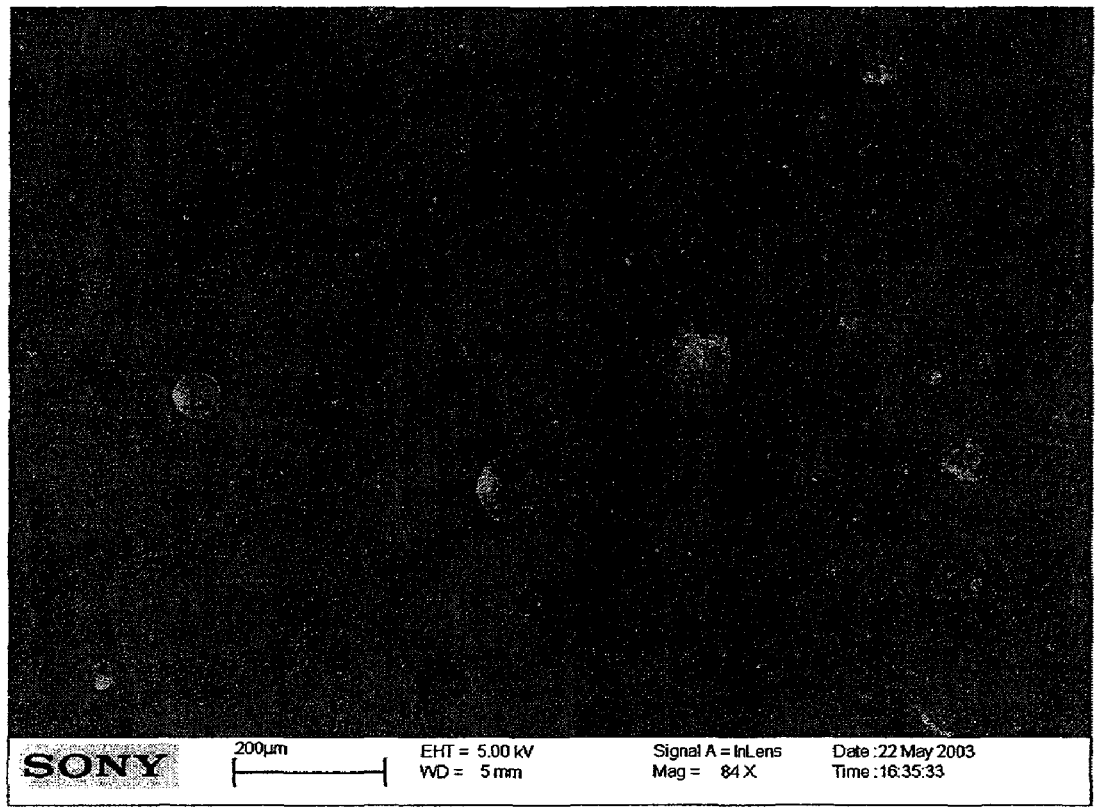
FIG. 7 shows an SEM image of the substrate from Example 4 (control) (scale bar 3 µm).

A Si(100) substrate (n-doped with native oxide surface) was treated in the $O_2$-plasma etcher for 5 min at 0.3 mbar. Subsequently it was dipped for 1 min in a HF solution (HF: $H_2O$ 1:50) and dried with compressed air (Step 1). The substrate was treated for 10 min with acetone and dried with compressed air. A PDMS stamp (Sylgard 184, Dow Corning) was placed for 10 min into an amine-terminated dendrimer ink solution and dried with compressed air. The ink solution was prepared by diluting 10-fold a commercially available solution of the dendrimers (Starburst® (PAMAM) Dendrimer, Generation 4, 10 wt. % solution in methyl alcohol, calculated FW 14,215, from Aldrich Chemical Co., Product #41,244-9). Subsequently the stamp was placed on the modified silicon substrate for 10 min (Step 4). Afterwards the substrate was washed with methanol and dried with compressed air (Step 5). As can be seen from FIG. 7, no pattern was transferred to the substrate. This control experiment demonstrates that surface activation with cyanuric chloride is required for printing a nucleophilic reagent such as amine-terminated dendrimer.

Example 5

Figure 8:
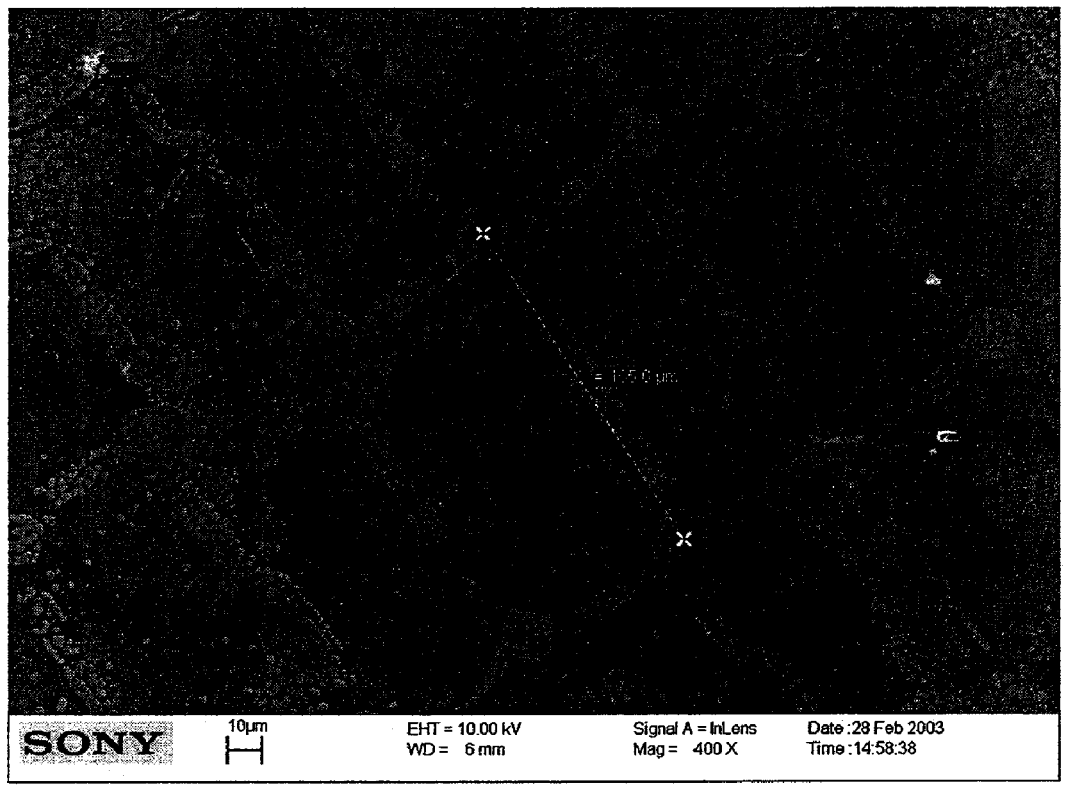
FIG. 8 shows an SEM image of the substrate from Example 5 (scale bar 10 µm).

A Si(100) substrate (n-doped with native oxide surface) was treated in the $O_2$-plasma etcher for 5 min at 0.3 mbar. Subsequently it was dipped for 1 min in a HF solution (HF: $H_2O$ 1:50) and dried with compressed air (Step 1). A stamp was inked with a solution of cyanuric chloride and N-ethyldiisopropylamine in acetone (100 mg cyanuric chloride, 100 µl N-ethyldiisopropylamine in 800 µl acetone) and washed with acetone and dried with compressed air (Step 3). The stamp was placed for 30 min on the substrate with a weight of 347 mg (Steps 2 and 4). After the pattern transfer process the substrate was washed with acetone. Subsequently the substrate was put into a solution of 4,7,10-trioxa-1,13-tridecanediamine (22 µl in 2 ml dichloromethane) for 30 min, in order to perform a nucleophilic substitution reaction on the patterned activated substrate. The substrate was washed with dichloromethane and dodecylamine stabilized Au-NPs were used for visualizing the amino functionalities of the transferred pattern. FIG. 8 shows an SEM image of the Si-substrate. The transferred pattern, which is a grid consisting of lines ~10 µm wide and ~100 µm long, is not perfect. The imperfections are partly due to the fact that the stamp was not perfect and the applied force during the printing process was too high. In addition, the PDMS in the stamp reacts with cyanuric chloride in the presence of the base N-ethyldiisopropylamine. Optimizing the inking time (Step 3) and the pattern transfer time (Step 4) are likely to lead to an improved pattern transfer.

Although a single type of substrate (n-doped Si(100) with native oxide surface) was used in these examples, the process is also applicable to Si(110) or Si(111) substrates as well and insensitive to the nature of doping. The thickness of the oxide layer is not an important factor since the layer is removed in Step 1.

Example 6

Electrode structures (5 nm Cr and 50 nm Au) were prepared on a Si wafer with a 500 nm thermally grown $SiO_2$ layer. The substrates were cleaned with an $O_2$ plasma cleaner (Gala instruments) at an oxygen pressure of 0.4 mbar and 33 W for 5 minutes. Subsequently the wafer was exposed for 1 min. to a 1% HF solution. The electrode structures remained unchanged, however, a slight, yet tolerable under etch was visible, meaning that this substrate can be used very well for subsequent activation through cyanuric chloride and the patterning process according to the present invention.

The features of the present invention disclosed in the specification, the claims and/or in the accompanying drawings, may, both separately, and in any combination thereof, be material for realising the invention in various forms thereof.

What we claim is:

1. A pattern of molecules on a silicon surface produced by a method comprising activating a silicon surface for subsequent patterning of molecules onto said surface, comprising:
    a) treatment of said silicon surface with HF,
    b) treatment of said silicon surface resulting from a) with cyanuric chloride,
    c) providing molecules to be patterned onto said silicon surface,
    d) applying said molecules to be patterned onto said silicon surface resulting from step b), wherein b) occurs in the presence of a base.

2. The pattern according to claim 1, wherein c) and d) are performed by
    providing a stamp and inking said stamp with an ink containing said molecules to be patterned and optionally a solvent for said molecules, thereby producing an inked stamp,
    placing said inked stamp on said silicon surface.

3. The pattern according to claim 2, wherein said inking is immersion inking comprising immersing said stamp into said ink or by placing said ink onto said stamp.

4. The pattern according to claim 2, wherein said inking is contact inking comprising placing said stamp on an ink pad that has previously been treated with said ink, or by placing an ink pad that has previously been treated with said ink onto said stamp.

5. The pattern according to claim 2, wherein said stamp is made of an elastic material having a Young's modulus in the range of 1 MPa to 50 MPa.

6. The pattern according to claim 2, wherein said method further comprises after placing said ink stamp on said silicon surface,
    e) leaving said inked stamp on said silicon surface for a time in the range of 1 s to 12 h and, optionally, applying pressure onto said inked stamp,
    f) withdrawing said stamp from said silicon surface.

7. The pattern according to claim 6, wherein said method further comprises, after d) and, f):
    g) rinsing said silicon surface with a solvent,
    h) exposing said silicon surface to compounds containing nucleophilic groups to passivate said silicon surface, or to introduce functional groups into said silicon surface.

8. The pattern according to claim 7, wherein said solvent is an inert solvent.

9. The pattern according to claim 7, wherein said compound containing nucleophilic groups is selected from the group consisting of ammonia, primary amines, secondary amines, water, alcohols, phenols, thiols and mercaptans.

10. The pattern according to claim 1, wherein said method further comprises, after d):
    i) rinsing said silicon surface with a solvent,
    j) exposing said silicon surface to compounds containing nucleophilic groups to passivate said silicon surface, or to introduce functional groups into said silicon surface.

11. The pattern according to claim 10, wherein said solvent is an inert solvent.

12. The pattern according to claim 10, wherein said compound containing nucleophilic groups is selected from the group consisting of ammonia, primary amines, secondary amines, water, alcohols, phenols, thiols and mercaptans.

13. The pattern according to claim 1, wherein said silicon surface resulting from b) is exposed to cyanuric chloride, over its entire area or at least over a substantial part of its area involving also regions not intended to be covered by said molecules to be patterned.

14. The pattern according to claim 13, wherein exposing said surface to cyanuric chloride occurs by immersion of said silicon surface into a solution of cyanuric chloride or by dripping or depositing a solution of cyanuric chloride onto said surface.

15. The pattern according to claim 1, wherein b) is performed by
    ba) providing a stamp and inking said stamp thereby producing an inked stamp,
    bb) placing said inked stamp on said silicon surface.

16. The pattern according to claim 15, where said ink does not comprise said molecules to be patterned on said silicon surface.

17. The pattern according to claim 15, wherein
    bc) said inked stamp is withdrawn from said silicon surface.

18. The pattern according to claim 17, wherein, after bc),
    bd) said silicon surface is rinsed with a solvent, preferably an inert solvent.

19. The pattern according to claim 18, wherein, after bd), c) and d) are performed by exposing said silicon surface to said molecules to be patterned.

20. The pattern according to claim 19, wherein said silicon surface is exposed to said molecules to be patterned, over its area entire area or at least over a substantial part of its area involving also regions not intended to be covered by molecules to be patterned.

21. The pattern according to claim 19, wherein exposing said silicon surface to said molecules to be patterned, occurs by immersion of said silicon surface into a composition of said molecules, or by dripping or depositing said molecules onto said surface.

22. The pattern according to claim 1, wherein said base is selected from the group consisting of sterically hindered tertiary organic amines and phosphazene bases.

23. The pattern according to claim 22, wherein said base is selected from the group consisting of N-ethyldiisopropylamine, N,N-diisopropylisobutylamine, tributylamine, 2,2,6,6-tetramethylpiperidine, N,N,N',N'-tetramethyl-1,8-napthalenediamine, 2,4,6-tri-tert-butylpyridine, tert-butyliminotris-(dimethylamine)-phosphorane, and tert-butylimino-tri-pyrrolidino-phosphorane.

24. The pattern according to claim 22, wherein said base is at a concentration in the range of 0% to 10 wt. %.

25. The pattern according to claim 1, wherein said base is at a concentration in the range of from 0-10 wt. %.

26. The pattern according to claim 1, wherein said molecules to be patterned are molecules containing nucleophilic groups.

27. The pattern according to claim 26, wherein said molecules containing nucleophilic groups are selected from the group comprising ammonia, primary amines, secondary amines, water, alcohols, phenols, thiols and mercaptans.

28. The pattern according to claim 1, wherein said molecules containing nucleophilic groups are in solution and at a concentration in the range of 1 µM-100 mM.

29. The pattern according to claim 1, wherein said silicon surface used for a) has been pre-patterned with gold electrode structures.

30. The pattern according to claim 1, wherein said silicon surface has a (100) or (110) or (111) surface orientation.

31. The pattern according to claim 1, wherein said silicon surface has a native or thermally grown oxide layer on it.

32. The pattern according to claim 1, wherein said silicon surface is part of a silicon substrate that is doped (n-type or p-type) or undoped.

33. The pattern according to claim 1, wherein said treatment of said silicon surface with HF (step a)) is done by treating said silicon surface with aqueous HF that may contain HCl.

34. The pattern according to claim 33, wherein said aqueous HF has a concentration that lies in the range of 0.06 M to 6 M and said HCl has a concentration that lies in the range of 0.01 M to 10 M.

35. The pattern according to claim 33, wherein said treatment with aqueous HF occurs for 0.1-10 minutes at 0° C. to 90° C.

36. The pattern according to claim 33, wherein said silicon surface has a (100) or (110) surface orientation.

37. The pattern according to claim 1, wherein said treatment of said silicon surface with HF is done by treating said silicon surface with aqueous $NH_4F$ that may contain $NH_4OH$.

38. The pattern according to claim 37, wherein said aqueous $NH_4F$ has a concentration that lies in the range of 0.1-11 M and said $NH_4OH$ has a concentration that lies in the range of 0.01 M to 10 M.

39. The pattern according to claim 37, wherein said treatment with aqueous $NH_4F$ occurs for 0.1-10 min at 0° C. to 90° C.

40. The pattern according to claim 37, wherein said silicon surface has a (111) surface orientation.

41. The pattern according to claim 1, where said treatment with cyanuric chloride (step b)) is performed using a solution of cyanuric chloride at a concentration in the range of from 0.1-10 wt. %.

42. The pattern according to claim 1, wherein said treatment with cyanuric chloride is performed over 1-100 min at 0-50° C.

43. The pattern according to claim 1, wherein the activated silicon surface, after activation by cyanuric chloride, is H-terminated in a proportion of its surface area.

44. An electronic device, a memory device, a photonic device, an energy conversion device, a display device, a sensor device, a biochip, an actuator, an electromechanical device or a microfluidic device comprising the pattern of molecules on a silicon surface according to claim 1.

* * * * *